(12) United States Patent
Yang et al.

(10) Patent No.: US 11,253,691 B2
(45) Date of Patent: Feb. 22, 2022

(54) INTRA-AORTIC DUAL BALLOON DRIVING PUMP CATHETER DEVICE

(71) Applicant: FUWAI HOSPITAL OF CHINESE ACADEMY OF MEDICAL SCIENCES, Beijing (CN)

(72) Inventors: Yuejin Yang, Beijing (CN); Yi Mao, Beijing (CN)

(73) Assignee: FUWAI HOSPITAL OF CHINESE ACADEMY OF MEDICAL SCIENCES, Beijing (CN)

( * ) Notice: Subject to any disclaimer, the term of this patent is extended or adjusted under 35 U.S.C. 154(b) by 0 days.

(21) Appl. No.: 16/843,216

(22) Filed: Apr. 8, 2020

(65) Prior Publication Data
US 2021/0138129 A1    May 13, 2021

(30) Foreign Application Priority Data
Nov. 8, 2019  (CN) .......................... 201911086298.1

(51) Int. Cl.
*A61M 1/10*        (2006.01)
*A61M 60/135*      (2021.01)
(Continued)

(52) U.S. Cl.
CPC ........ *A61M 60/135* (2021.01); *A61M 60/432* (2021.01); *A61M 60/50* (2021.01);
(Continued)

(58) Field of Classification Search
CPC ............ A61M 2205/32; A61M 60/135; A61M 60/40; A61M 60/833; A61M 60/857
See application file for complete search history.

(56) References Cited

U.S. PATENT DOCUMENTS 4,697,574 A   10/1987   Karcher et al.
4,902,272 A    2/1990   Milder et al.

FOREIGN PATENT DOCUMENTS

CN    105816926 A    8/2016
CN    108525107 A    9/2018
(Continued)

OTHER PUBLICATIONS

Extended European Search Report for related European Patent Application No. 19214736.1 dated Jun. 30, 2020 (7 pages).
(Continued)

*Primary Examiner* — Jon Eric C Morales
(74) *Attorney, Agent, or Firm* — Procopio, Cory, Hargreaves & Savitch LLP

(57) ABSTRACT

An intra-aortic dual balloon driving pump catheter device having a catheter; a first balloon and a second balloon respectively surrounding the catheter, being arranged successively along the longitudinal direction of the catheter, wherein the position of the first balloon is placed at the distal end of the catheter, and the second balloon is placed immediately adjacent to the proximal end of the first balloon; the first balloon and the second balloon are periodically expanded to a dimension that nearly blocks the aortic blood flow and contracted to a dimension that does not prevent the blood flow from passing through; wherein the first balloon periodically inflates in diastole and deflates in systole working as a pump, while the second balloon conversely deflates in systole and inflates in diastole functioning as a valve, altogether leading to blood pumping from contracting ventricle and keeping driving forward ahead in the aorta.

8 Claims, 2 Drawing Sheets

(51) Int. Cl.
    *A61M 60/857*     (2021.01)
    *A61M 60/432*     (2021.01)
    *A61M 60/50*     (2021.01)
    *A61M 25/10*     (2013.01)

(52) U.S. Cl.
    CPC ....... *A61M 60/857* (2021.01); *A61M 25/1011* (2013.01); *A61M 2230/04* (2013.01)

(56) References Cited

FOREIGN PATENT DOCUMENTS

| | | |
|---|---|---|
| JP | H05-212109 A | 8/1993 |
| JP | H05212109 A | 8/1993 |
| JP | 2007-265412 A | 10/2007 |
| JP | 2010-155909 A | 7/2010 |
| JP | 2016-524937 A | 8/2016 |
| JP | 202174483 A | 5/2021 |

OTHER PUBLICATIONS

Office Action for related Japanese Patent Application No. 2019-223111, dated Oct. 6, 2020 (2 pages).
Japan Decision on Patent JP20578 dated May 11, 2021 granting Japanese application 2019-223111 [Foreign Reference 1] (3 pages).
Chinese Patent Office, Office Action, Application No. CN201911086298.1, dated May 28, 2021, in 8 pages.
Response to First Office Action, Application No. 2019-110862981, dated May 28, 2021, in 23 pages.
National Intellectual Property Administration of China, Notification of Second Office Action, Application No. 201911086298.1, dated Dec. 22, 2021, in 17 pages.

INTRA-AORTIC DUAL BALLOON DRIVING PUMP CATHETER DEVICE

CROSS-REFERENCE TO RELATED APPLICATIONS

This application claims priority to Chinese Patent Application No. 201911086298.1, filed on Nov. 8, 2019, the contents of which are incorporated herein by reference.

TECHNICAL FIELD

The present invention relates to an intra-aortic dual balloon driving pump catheter device.

BACKGROUND ART

Intra-aortic balloon pump (IABP) is a mechanically assistive circulatory device widely and effectively used in the current clinical application. It is a cardiac catheterization therapy wherein a catheter with a balloon is placed through the arterial system to the proximal end of the heart within the descending thoracic aorta, or an end distal to the left subclavian artery opening, inflating and deflating of the balloon correspondingly to the cardiac cycle such that the blood flow changes in time phase within the aorta so as to mechanically assist the circulation. The aim is thus achieved to reduce aortic impendence and to increase cardiac output and aortic diastolic pressure while reducing myocardial oxygen consumption and increasing oxygen supply, so as to improve the function of the heart.

The intra-aortic balloon pump (IABP) may be applied to different situations to improve the patient's hemodynamics by increasing coronary artery perfusion and reducing afterload of ventricle. These factors improve the heart function and myocardial oxygen demand-supply ratio. Its role is quite mild, and generally the cardiac output does not increase by more than 20%. The indications of intra-aortic balloon pump (IABP) include the following three situations: treatment of acute myocardial ischemia, postoperative cardiogenic shock, transition before cardiac transplantation, and etc.

The intra-aortic balloon pump device comprises a balloon catheter, and a counterpulsation machine serving as a driving section of the balloon catheter. The balloon catheter consists of an air supply catheter and a cylindrical balloon secured to the catheter. The standard for selecting the balloon catheter is to block 90%-95% of the aortic lumen after the balloon is inflated, and the balloon volume is greater than 50% of the heart's stroke volume. The counterpulsation machine comprises a monitoring part, a controlling part, a vacuum pump, and an air compressor. The air supply catheter communicates the elongated cylindrical balloon with the vacuum pump and the air compressor. The monitoring part and the controlling part cooperates with each other to automatically identify the ECG or pressure signal according to the given parameters, automatically regulate the time phase of inflation and deflation, and automatically adjust the counterpulsation parameters so as to achieve the best counterpulsation effect, and automatically stop when there is a failure or abnormal stroke.

The balloon is inflated when the heart dilates, and the balloon is deflated when the heart contracts. The double effect of hemodynamics is thus produced. On one hand, the balloon is inflated in the diastole, so as to occupy the space of the blood. In this case, as the aortic valve has closed, so that the inflated balloon quickly drives blood to both the distal and the proximal sides of the aorta, whereby driving blood to the distal (cordis) side increases the diastolic pressure at the aortic root, and thus increases the coronary artery blood and the myocardial oxygen supply; and driving blood to the proximal (peripheral) side increases whole body perfusion, and thus increases the diastolic pressure and support the cardiac circulation. The increase of the diastolic pressure greatly lowers the work load of the heart, particularly the left ventricle, and the blood supply is greatly improved. On the other hand, the balloon is deflated during the systole to lower the systolic pressure (cardiac afterload), so as to produce negative pressure, whereby the aortic pressure is reduced instantly, the ejection resistance and the cardiac afterload lowered, the cardiac output increased, and the myocardial oxygen consumption reduced. The decrease in ejection resistance improves the left ventricular ejection. In this case, the blood is inhaled into the aorta, the aortic pressure is lowered and the cardiac afterload is reduced. The controlling part is able to adjust the size of the balloon by controlling the air amount entering the balloon.

The counterpulsation of the balloon is usually triggered by the arterial waveform recorded at the top of the balloon, or is controlled by the electrocardiogram QRS waveform with time. The balloon counterpulsation must be inflated and deflated within accurate time period. Ideally, the balloon shall be inflated when the aortic valve is just closed, corresponding to the trace between two ascending waves of arterial waveform. Meanwhile, it is preferable that the balloon is deflated before the left ventricle is about to eject. Premature deflation in diastole may bring poor efficacy.

The current clinical IABP catheter can be only inflated and deflated by its balloon corresponding to the cardiac cycle to cause change in time phase of the blood within the aorta, but cannot actively drive the blood.

SUMMARY OF THE INVENTION

Therefore, it is required to provide an IABP catheter which may further proactively drive forward the blood.

Said technical problem may be solved by the present invention providing an intra-aortic dual balloon driving pump catheter device. The intra-aortic dual balloon driving pump catheter device comprises: a catheter; a first balloon and a second balloon, the first balloon and the second balloon surrounding the catheter, being arranged successively along the longitudinal direction of the catheter, wherein the first balloon is a counterpulsation balloon, being placed at the distal end of catheter, and the second balloon is a valve balloon, being placed immediately adjacent to the proximal end of the first balloon and is closer to the proximal end of the catheter than the first balloon; a monitoring part, for monitoring the cardiac cycle and the arterial pressure of the catheter end; air pumps, respectively associated with the first balloon and the second balloon for supplying and withdrawing air; a first intake pipe and a second intake pipe, one end of which is in communication with the first balloon and the second balloon respectively, and the other end of which is in communication with the respectively associated air pump; a controlling part, adapted to control the air pumps to inflate and deflate the first balloon and the second balloon according to the cardiac cycle and the arterial pressure of the catheter end monitored by the monitoring part, such that the first balloon periodically inflates in diastole to occupy the space of blood in aorta, so as to push blood towards both sides of the first balloon, whereas deflates in systole to create space, so as to proactively extract pumped-out blood from the heart, and thus increases the cardiac output; and the second balloon inflates in systole to block the distal end of the aorta to prevent the blood flow at the distal end of the aorta from returning when the first balloon deflates, and deflates in diastole to make the blood flow created by the inflation of the first balloon be pushed forward downstream.

In diastole, the first balloon inflates and the second balloon deflates, which brings the following effects: the inflation of the first balloon per se drives the blood to both the distal (cordis) and the proximal (peripheral) sides of the aorta, so that the diastolic pressure at the aortic root is increased, thereby increasing the coronary artery blood and myocardial oxygen supply, and also promoting peripherally the blood supply and perfusion to the whole body.

In systole, the first balloon deflates and the second balloon inflates, which brings the following blood-driving effects: deflating the first balloon causes rapidly blood space emptying and pressure decreasing in the aorta, and then blood sucked into the aorta from the ejecting heart, which remarkably pumps upstream heart blood into the aorta due to the maximal pressure difference between the ejecting heart and the emptied aorta generated by the combination of the first balloon deflating and the second balloon blocking to stop blood reflux, and thus drives the blood forward downstream ahead in diastole of the next cardiac cycle. As a result, the blood circulation will be not only intensified, pushed and driven, but also kept in the unidirectional forward ahead, which can actively and strongly support the normal circulation state for circulatory failure or even collapse.

According to an embodiment of the intra-aortic dual balloon driving pump catheter device according to the present invention, the air pumps are controlled such that the second balloon deflates at the same time the first balloon inflates, whereas the second balloon inflates at the same time the first balloon deflates. In each cardiac cycle, the second balloon deflates and inflates conversely to the synchronized inflation and deflation of the first balloon.

Advantageously, the intra-aortic dual balloon driving pump catheter device according to the present invention permits, in particular situations, the air pumps to be controlled such that the first balloon and the second balloon inflate and deflate at the same time, or rather the second balloon keeps deflated, without inflation, as with an ordinary IABP.

Importantly, in any case, it is always not allowable for the second balloon not to deflate but only inflate, and thus blocks the aorta.

The first balloon and the second balloon are in communication with the respectively associated air pump via a first intake pipe and a second intake pipe. There may be multiple embodiments for the arrangement of the intake pipes and the catheter.

According to an embodiment of the intra-aortic dual balloon driving pump catheter device according to the present invention, the first intake pipe surrounds the catheter and extends together therewith through the second balloon. Preferably, after extending through the second balloon, the first intake pipe and the catheter surrounded by the first intake pipe extend in parallel with the second intake pipe. Or, in another preferable embodiment, after extending through the second balloon, the first intake pipe is surrounded by and extends together with the second intake pipe.

According to another embodiment of the intra-aortic dual balloon driving pump catheter device according to the present invention, after extending through the second balloon respectively, the catheter and the first intake pipe extend in parallel with the second intake pipe.

According to an embodiment of the intra-aortic dual balloon driving pump catheter device according to the present invention, the first balloon has a length longer than that of the second balloon. The first balloon and the second balloon play different roles in the process of successive actions. The first balloon is mainly to work as a counter-pulsation balloon for blood pump, while the second balloon to a valve balloon to stop blood reflux when the first balloon deflation for the blood to move downstream forward. The volume expanded by inflation of the first balloon determines the effects of sucking the upstream heart blood into aorta and driving the aorta blood to move downstream ahead. A shorter second balloon helps to stop blood reflux as a "valve" during the first balloon deflation and to promote more blood downstream when it is deflated.

Preferably, the first balloon has a length that is nine-tenth of a total length of the first balloon and the second balloon.

Figure 1:
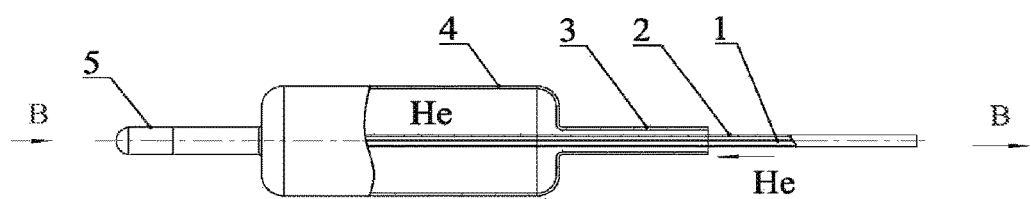
FIG. 1 shows an intra-aortic balloon pump catheter device of the prior art, which has only one balloon.

LIST OF REFERENCE SIGN 1 guide wire
2 catheter
3 first intake pipe
4 first balloon
5 catheter end
6 second balloon
7 second intake pipe

DETAILED DESCRIPTION OF THE PREFERRED EMBODIMENTS

The intra-aortic dual balloon driving pump catheter device of the present invention will be described in detailed embodiments with reference to the accompanying drawings. It shall be noted that the accompanying drawings are given by way of illustration only, and shall not be construed as limiting the present invention.

The intra-aortic dual balloon driving pump catheter device is guided by a guide wire 1 of a catheter 2 and reaches a predetermined position within the aorta, and then the guide wire 1 exits from the catheter 2.

Figure 2:
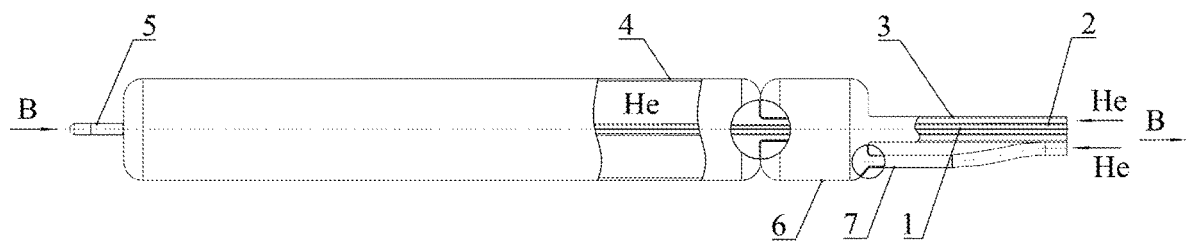
FIG. 2 shows a partial section view of an intra-aortic dual balloon driving pump catheter device according to the first embodiment of the present invention.

FIG. 2 shows a partial section view of an intra-aortic dual balloon driving pump catheter device according to the first embodiment of the present invention. As shown in the figure, a first balloon 4 and a second balloon 6 are arranged to successively surrounding the catheter 2 along the longitudinal direction of the catheter 2, wherein the position of the first balloon 4 is closer to a distal end of catheter 5 than the position of the second balloon 6. A first intake pipe 3 and a second intake pipe 7 have one end in communication with the first balloon 4 and the second balloon 6 respectively, and the other end in communication with the air pump (not shown) respectively associated with the balloons and used for supply and withdrawal of air.

The intra-aortic dual balloon driving pump catheter device according to the first embodiment of the present invention further comprises a monitoring part and a controlling part that are not shown in the figure. The monitoring part is used for monitoring the cardiac cycle and the arterial pressure of the catheter end 5, while the controlling part is adapted to control the air pumps to inflate and deflate the first balloon 4 and the second balloon 6 according to the cardiac cycle and the arterial pressure of the catheter end 5 monitored by the monitoring part, such that the first balloon 4 periodically inflates in diastole to occupy the space of blood in aorta, so as to push blood towards both sides of the first balloon, whereas deflates in systole to create space, so as to proactively extract pumped-out blood from the heart, and thus increases the cardiac output; and the second balloon inflates in systole to block the distal end of the aorta to prevent the blood flow at the distal end of the aorta from returning when the first balloon deflates, and deflates in diastole to make the blood flow created by the inflation of the first balloon be pushed forward downstream.

In this embodiment, the first intake pipe 3 protruding from the first balloon 4 surrounds and extends together with the catheter 2 through the second balloon 6, and then extends in parallel with the second intake pipe 7 protruding from the second balloon 6. An air pump associated with the first intake pipe 3 and the second intake pipe 7 respectively may supply, for example, helium gas into the first balloon 4 and the second balloon 6 to inflate the latter. The whole process of inflation is required to be completed within 130 ms. However, the air pumps are controlled such that the first balloon 4 inflates in diastole and deflates in systole, while the second balloon 6 deflates in systole and inflates in diastole. In diastole, the inflation of the first balloon 4 synchronizes with the deflation of the second balloon 6; in systole, the deflation of the first balloon 4 synchronizes with the inflation of the first balloon 6.

In diastole, the inflation of the first balloon 4 per se drives the blood to both the distal (cordis) and the proximal (peripheral) sides of the balloon in aorta, so that the diastolic pressure at the aortic root and coronary artery blood and myocardial oxygen supply are increased, and the blood is also simultaneously pushed downstream forward ahead to supply the whole body.

In systole, the first balloon 4 deflates to suck more blood from ejecting heart into the aorta, while the second balloon 6 simultaneously inflates to stop blood reflux, which results in pumping more blood from the heart and driving downstream forward when the second balloon 6 deflates in the next cardiac cycle, and therefore supporting effectively and strongly the normal circulation status for circulatory failure or even collapse.

Before the systole is about to begin, the air pump withdraws the air from the first balloon 4 and the second balloon 6 so that the balloons are deflated at the same time. The blood is withdrawn from the ejecting heart by the negative pressure and enters into the space in the aorta produced by the contraction, whereby the ejection resistance and the cardiac afterload are lowered, and the cardiac output is increased as with an ordinary IABP.

Herein, the air pumps are controlled such that the inflation and the deflation of the first balloon 4 synchronizes with the deflation and the inflation of the second balloon. However, the air pumps may also be controlled such that the second balloon 6 has already started to deflate when the first balloon 4 begins to inflate. The desired technical effect may be achieved as long as the inflation and the deflation of the second balloon 6 conversely synchronizes with the inflation and the deflation of the first balloon 4. Nevertheless, it is not allowed for the second balloon not to deflate but only inflate, and thus blocks the aorta.

Figure 3:
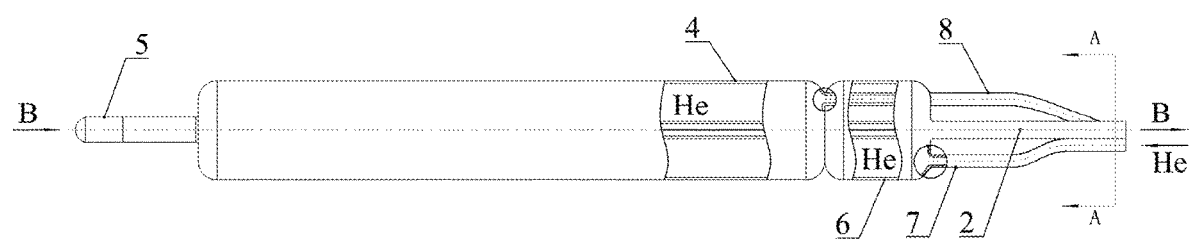
FIG. 3 shows a partial section view of an intra-aortic dual balloon driving pump catheter device according to the second embodiment of the present invention.
Figure 4:
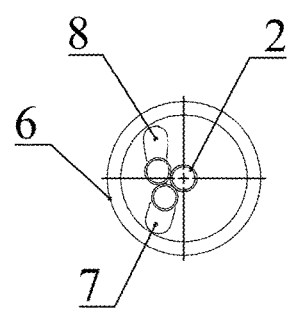
FIG. 4 shows a cross section view seen from line A-A in FIG. 3.

FIG. 3 shows a partial section view of an intra-aortic dual balloon driving pump catheter device according to the second embodiment of the present invention. FIG. 4 shows a cross section view seen from line A-A in FIG. 3. It differs from the first embodiment of the present invention in that: the first intake pipe 3 protruding from the first balloon 4 does not surround the catheter 2 through the first balloon 4 and the second balloon 6, but passes through the second balloon 6 individually. The first intake pipe 3 through the second balloon 6, the catheter 2, and the second intake pipe 7 protruding from the second balloon 6 extend in parallel with each other as shown in the figure.

While the present invention has been described with reference to the preferred embodiments, the spirit and scope of the invention are not limited to the disclosure herein. According to the teaching of the present invention, those skilled in the art are able to deduce more embodiments and applications without departing from the spirit and scope of the present invention, which are not defined by the embodiments but by the appended claims.

What is claimed is that:

1. An intra-aortic dual balloon driving pump catheter device, which comprises:
    a catheter;
    a first balloon and a second balloon, respectively surrounding the catheter, being arranged successively along the longitudinal direction of the catheter, wherein the first balloon is a counterpulsation balloon, being placed at the distal end of the catheter, and the second balloon is a valve balloon, being placed immediately adjacent to the proximal end of the first balloon and is closer to the proximal end of the catheter than the first balloon;
    a monitoring part, for monitoring the cardiac cycle and the arterial pressure of the catheter end;
    air pumps, respectively associated with the first balloon and the second balloon, for supplying and withdrawing air;
    a first intake pipe and a second intake pipe, one end of which is in communication with the first balloon and the second balloon respectively, and the other end of which is in communication with the respectively associated air pump;
    a controlling part, adapted to control the air pumps to inflate and deflate the first balloon and the second balloon according to the cardiac cycle and the arterial pressure of the catheter end monitored by the monitoring part, such that the first balloon periodically inflates in diastole to occupy the space of blood in aorta, so as to push blood towards both sides of the first balloon, whereas deflates in systole to create space, so as to proactively withdraw ejecting blood from the heart, and thus increases the cardiac output; and the second balloon inflates in the systole to block the distal end of the aorta to prevent the blood reflux at the distal end of the aorta when the first balloon deflates, and deflates in the diastole to make the blood flow created by the inflation of the first balloon be pushed forward downstream,
    wherein the air pumps are controlled such that the second balloon deflates at the same time the first balloon inflates, whereas the second balloon inflates at the same time the first balloon deflates, so that in each cardiac cycle, the air pumps are controlled such that the second balloon deflates and inflates conversely to the synchronized inflation and deflation of the first balloon.

2. The intra-aortic dual balloon driving pump catheter device according to claim 1, characterized in that the first intake pipe surrounds the catheter and extends together therewith through the second balloon.

3. The intra-aortic dual balloon driving pump catheter device according to claim 2, characterized in that, after extending through the second balloon, the first intake pipe and the catheter surrounded by the first intake pipe extend in parallel with the second intake pipe.

4. The intra-aortic dual balloon driving pump catheter device according to claim 2, characterized in that, after extending through the second balloon, the first intake pipe is surrounded by and extends together with the second intake pipe.

5. The intra-aortic dual balloon driving pump catheter device according to claim 1, characterized in that, after extending through the second balloon, the first intake pipe is surrounded by and extends together with the second intake pipe.

6. The intra-aortic dual balloon driving pump catheter device according to claim 1, characterized in that, after extending through the second balloon respectively, the catheter and the first intake pipe extend in parallel with the second intake pipe.

7. The intra-aortic dual balloon driving pump catheter device according to claim 1, characterized in that the first balloon has a length longer than that of the second balloon.

8. The intra-aortic dual balloon driving pump catheter device according to claim 1, characterized in that the first balloon has a length that is nine-tenth of a total length of the first balloon and the second balloon.

* * * * *